United States Patent [19]

Sibalis

[11] Patent Number: 5,163,899
[45] Date of Patent: * Nov. 17, 1992

[54] TRANSDERMAL DRUG DELIVERY SYSTEM

[75] Inventor: Dan Sibalis, Stony Brook, N.Y.

[73] Assignee: Drug Delivery Systems Inc., New York, N.Y.

[*] Notice: The portion of the term of this patent subsequent to Jun. 17, 2008 has been disclaimed.

[21] Appl. No.: 453,045

[22] Filed: Dec. 12, 1989

Related U.S. Application Data

[63] Continuation of Ser. No. 257,196, Oct. 13, 1988, abandoned, which is a continuation of Ser. No. 28,679, Mar. 20, 1987, abandoned.

[51] Int. Cl.⁵ .............................................. A61N 1/30
[52] U.S. Cl. ....................................... 604/20; 128/798
[58] Field of Search ................. 128/82.1, 798, 802, 128/803; 604/20

[56] References Cited

U.S. PATENT DOCUMENTS

| | | | |
|---|---|---|---|
| 4,416,274 | 11/1983 | Jacobsen et al. | 604/20 |
| 4,557,723 | 12/1985 | Sibalis | 128/798 |
| 4,689,039 | 8/1987 | Masaki | 604/20 |

Primary Examiner—Randy C. Shay
Attorney, Agent, or Firm—Lackenbach Siegel Marzullo & Aronson

[57] ABSTRACT

An electro-osmotic transdermal drug delivery system for passing a drug to the systemic blood of a patient through the skin. The delivery system includes a semi-dry drug patch containing a water solute with the drug and a selected level of current delivered to the semi-dry patch. Water from the semi-dry patch is limited in movement from the patch to the skin particularly in lateral movement relative to the skin so that the sweat and sebaceous ducts and glands, which ordinarily are filled with liquid, namely the solute, and act as electrical shunts for osmotic delivery of the drug, are starved of liquid so that the electrical current is diverted to the stratum corneum along with the electro-osmotic movement of the liquid carrying the drug. This result greatly increases the total drug delivery area of the skin. In addition, because the current need not be kept at a low level to avoid irritation or damage to the skin shunts, the current of the invention can be significantly elevated so as to overcome the higher resistivity of the stratum corneum to the passage of liquid and current. A current conditioner such as an oscillator can be added to the system so as to break the liquid column of the skin shunts at periodic time intervals in accordance with natural replenishment and blow out of the skin shunts that will occur at relatively long time periods.

4 Claims, 4 Drawing Sheets

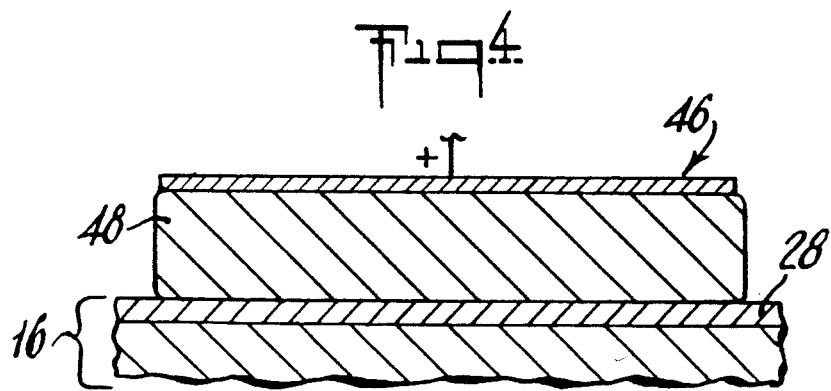
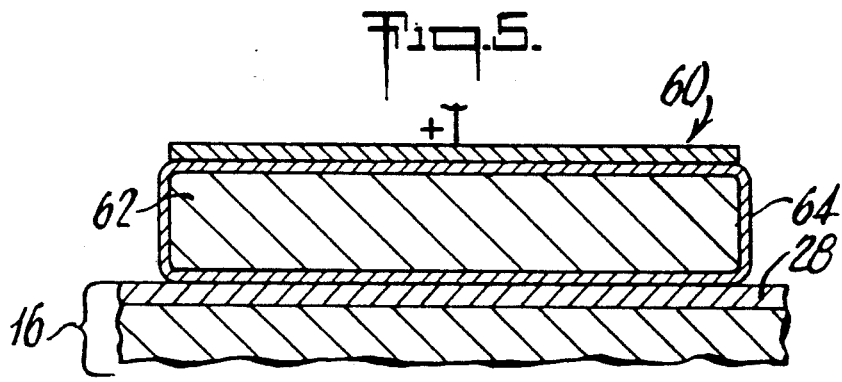
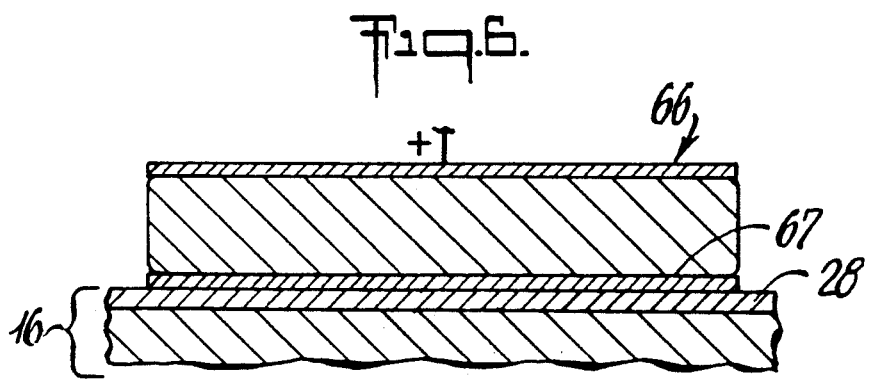
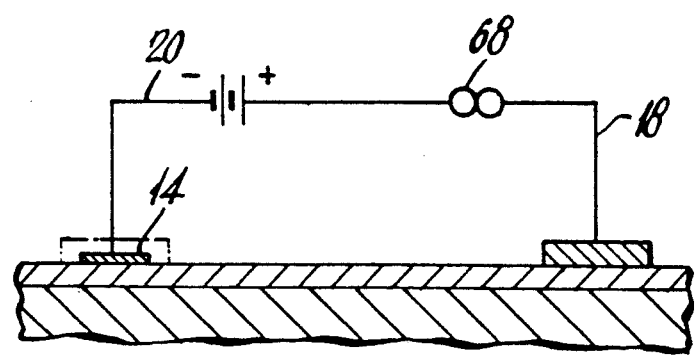

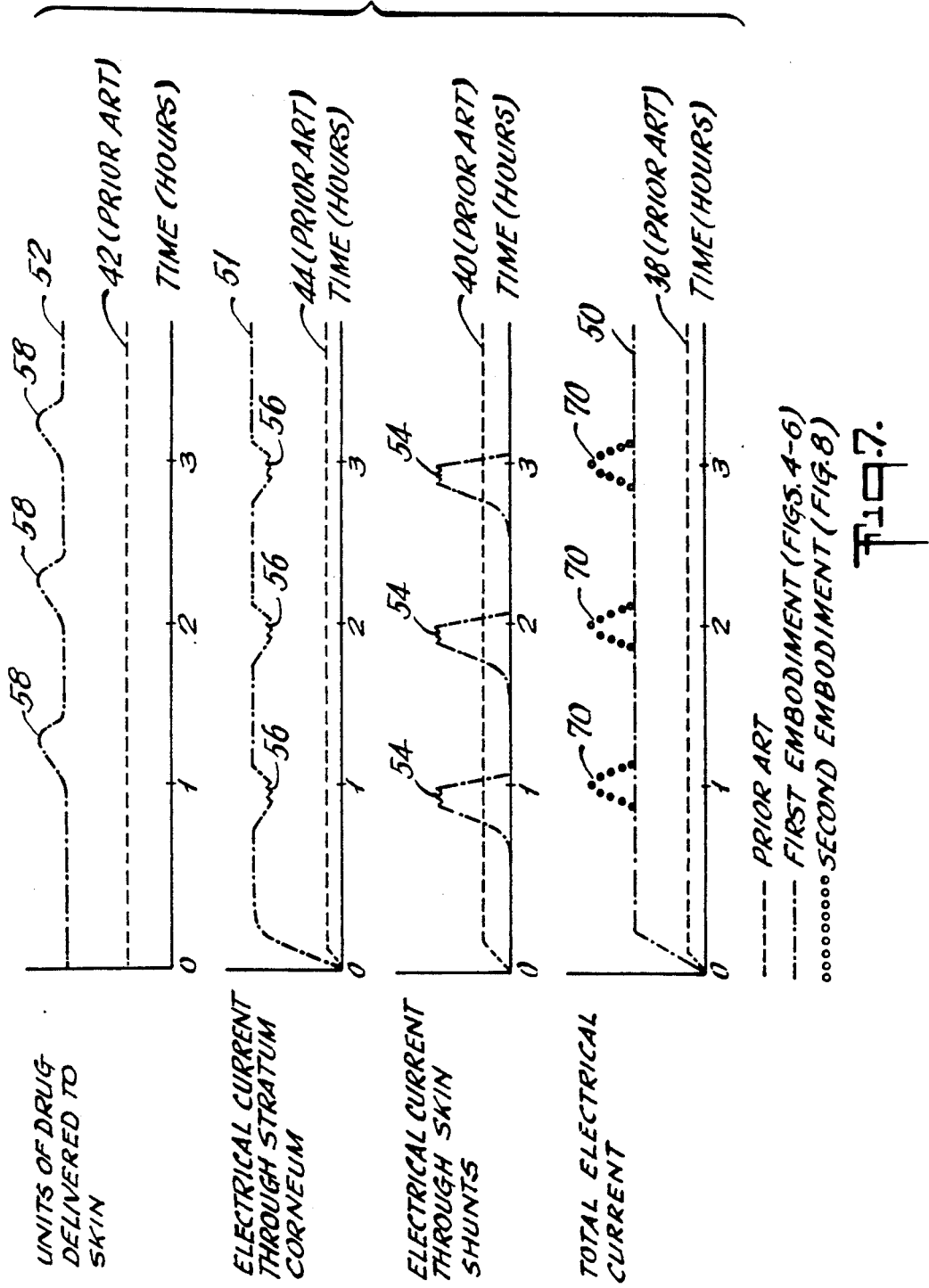

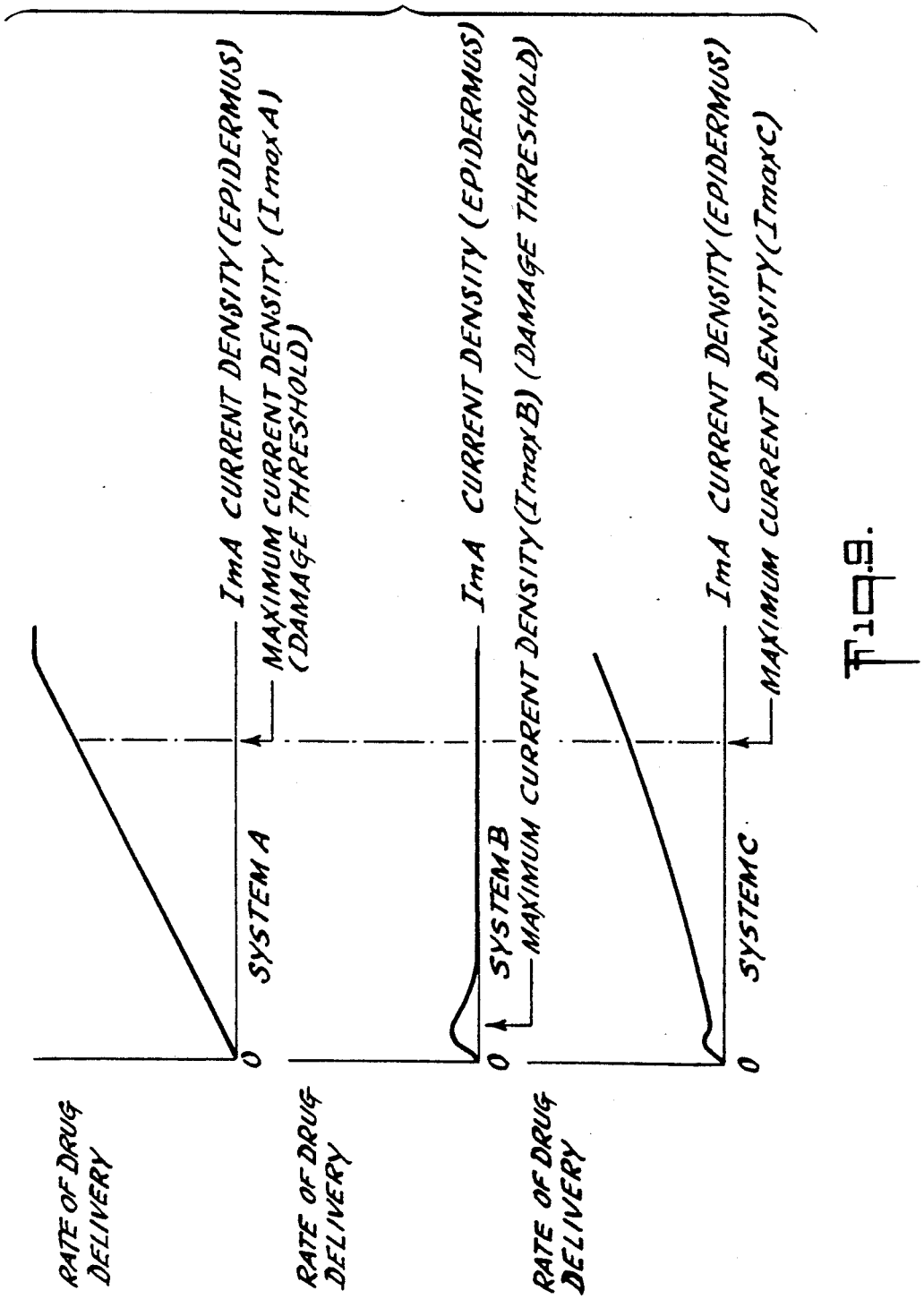

ns.3% TRANSDERMAL DRUG DELIVERY SYSTEM

RELATED U.S. PATENT APPLICATIONS

This application is a continuation of application Ser. No. 257,196, filed Oct. 13, 1988, now abandoned, which is a continuation of application Ser. No. 028,679, filed Mar. 20, 1987, now abandoned.

FIELD OF THE INVENTION

The present invention relates to transdermal drug delivery systems and more particularly to electro-osmotic transdermal drug delivery systems that function b passing an electrical current through skin that is in contact with a drug patch.

BACKGROUND OF THE INVENTION

Delivery of drugs to the systemic blood of a patient by means of an electro-osmotic transdermal system is accomplished primarily through the sweat and sebaceous ducts and their respective glands rather than through the stratum corneum. The skin of humans is covered by the stratum corneum, which, although very thin, is resistant to the passage of both current and of liquids. In addition, the sweat and sebaceous ducts, when filled with liquid, become paths of least electrical resistance and in effect become shunts, and are so-called herein, for the passage of electricity and thus for the passage of drugs contained in the drug patch, bypassing the stratum corneum. These shunts extend through the stratum corneum with their duct openings being at the surface of the stratum corneum; the duct openings occupy about one thousandth of the surface of the stratum corneum. The capillary shunts are very small in diameter being in the range of $10^{-3}$ cm$^2$ and are thus prone to being easily irritated and damaged by overheating and by excessive endosmotic pressure in the shunts by the passage of current through the shunts. Irritation of the shunts results in a tingling sensation and discomfort to the patient. Current density and the rate of drug delivery through the shunt ducts is thus limited not only by the small overall area that the shunts occupy relative to the area of the stratum corneum but also by the susceptibility of the shunts to damage because of the high current density.

Accordingly, it is an object of this invention to provide an electro-osmotic transdermal drug delivery system that primarily delivers a drug or drugs through the stratum corneum and substantially avoids drug delivery through the skin shunts so that the possibility of damage to the skin shunts is limited.

It is another object of this invention to provide an electro-osmotic transdermal drug delivery system that primarily delivers a drug or drugs through the stratum corneum so that the entire surface of the stratum corneum can be utilized for drug delivery with the result that the overall rate of drug delivery is improved as compared to the rate of drug delivery primarily through the skin shunts.

It is another object of this invention to provide an electro-osmotic transdermal drug delivery system that primarily delivers a drug or drugs through the stratum corneum so that a higher current can be used in the system than the current that could be used when drug delivery is primarily through the skin shunts with the result that the rate of drug delivery is enhanced relative to the rate of drug delivery primarily through the skin shunts.

SUMMARY OF THE INVENTION

In accordance with these and other objects there is provided an electro-osmotic transdermal drug delivery system for passing a drug or drugs to the systemic blood of a patient through the skin. The delivery system includes a semi-dry drug patch containing a water solute with the drug or drugs and a selected level of current delivered to the semi-dry patch. Water from the semi-dry patch is limited in movement from the patch to the skin particularly in lateral movement relative to the skin so that the sweat and sebaceous ducts and glands, which ordinarily are filled with liquid, namely the solute, and act as electrical shunts, are starved of liquid so that the electrical current is diverted to the stratum corneum along with the electro-osmotic movement of the liquid carrying the drug or drugs. This result greatly increases the total drug delivery area of the skin. In addition, because the current need not be kept at a low level to avoid irritation or damage to the skin shunts, the current density of the invention can be significantly increased so as to overcome the higher resistivity of the stratum corneum to the passage of liquid and current. A current conditioning device such as an oscillator can be added to the system so as to break the liquid capillary columns of the skin shunts at periodic time intervals in accordance with their natural replenishment and disable the conductivity of the skin shunts that will occur at relatively long time periods.

BRIEF DESCRIPTION OF THE DRAWINGS

FIG. 4 is a cross-sectional view of a drug patch comprising a drug or drugs contained in a relatively dry gel in contact with the skin of a patient;

FIG. 5 is a cross-sectional view of a drug patch comprising a wet reservoir surrounded by a semi-permeable membrane in contact with the skin of a patient;

FIG. 6 is a cross-sectional view of a drug patch comprising a drug or drugs contained in a matrix with a water-repelling agent present at the surface of the patch and the skin of the patient;

FIG. 7 is a model graph illustrating the principle of electro-osmotic drug delivery both in a prior art transdermal drug delivery system and two drug delivery systems in accordance with the present invention;

FIG. 8 is a schematic view of a transdermal drug delivery system similar to the system shown in FIG. 1 with any of the drug reservoirs shown in FIGS. 4–6 and also including an electrical oscillator; and FIG. 9 is a model graph illustrating a theoretical drug delivery system through the skin epidermis only [stratum corneum] devoid of skin shunts; through a skin comprising only skin shunts and devoid of a stratum corneum; and the model of a delivery through the human skin bypassing the skin shunts.

DESCRIPTION OF THE PREFERRED EMBODIMENTS

Reference is now made in detail to the drawings wherein the numerals refer to the same or similar elements throughout.

Figure 1:
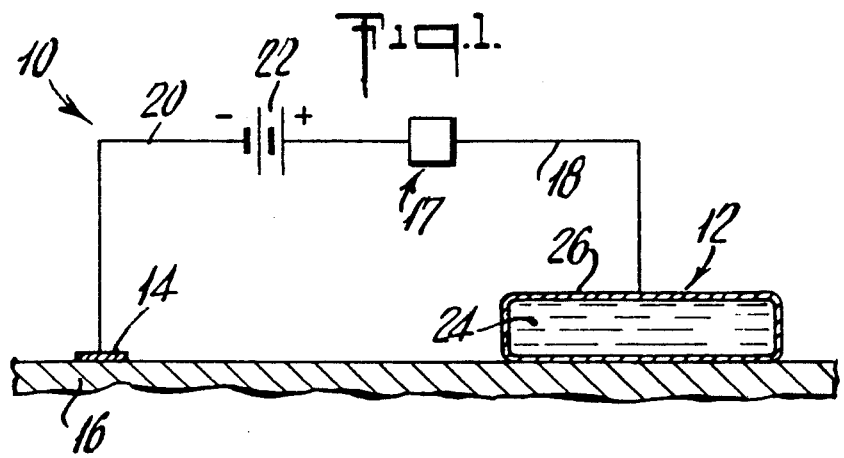
FIG. 1 is a schematic drawing of an electro-osmotic drug delivery system including a drug patch in osmotic contact with the skin of a patient.

An electro-osmotic drug delivery system 10 of the general type to which the present invention relates is shown in FIG. 1. Drug delivery system 10 includes a drug storage patch, shown as a reservoir 12, an electrode 14 each in contact with the skin 16 of a patient, and a current conditioner 17. Reservoir 12 and electrode 14 are connected by conductors 18 and 20, respectively, and to the positive and negative poles of battery 22, respectively. Reservoir 12 includes an electrolytic liquid suspension, or solution, 24, containing a drug or drugs to be delivered to the systemic blood of the patient. Solution 24 is contained by a permeable membrane 26, which is in contact with skin 16. The drug or drugs to be delivered to the patient is shown by way of example to be stored in the membrane-sealed drug reservoir 12, but the drug or drugs could be stored in a solute in a matrix, or hydrogel.

Figure 2:
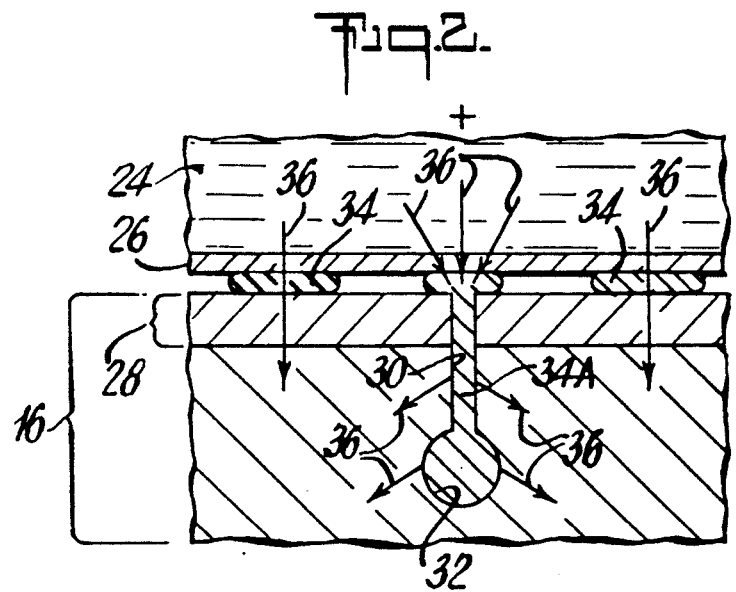
FIG. 2 is an isolated, enlarged, schematic cross-sectional of a drug patch delivering a drug or drugs by electro-osmosis to the body of a patient with drug delivery being made through an exemplary skin shunt with movement of the current and drug or drugs through the stratum corneum being relatively inactive.

FIG. 2 illustrates the manner in which the drug or drugs in solution 24 is passed by electro-osmosis through skin 16 to the systemic blood of the patient primarily through the sweat ducts and sebaceous ducts and their respective glands exemplified by shunt duct 30 and shunt duct gland 32. A liquid 34 originating at solution 24 joins a liquid column 34A in shunt duct 30 and the zone above shunt duct 30 with membrane 26 by way of electro-osmotic movement from solution 24 as indicated by arrows 36 to create an electrical path from membrane 26 to shunt duct 30 and gland 32. Shunt duct 30 thus becomes an electrical shunt of low resistance, especially as compared to the relatively high-resistance electrical path that is created through stratum corneum 28.

Figure 3:
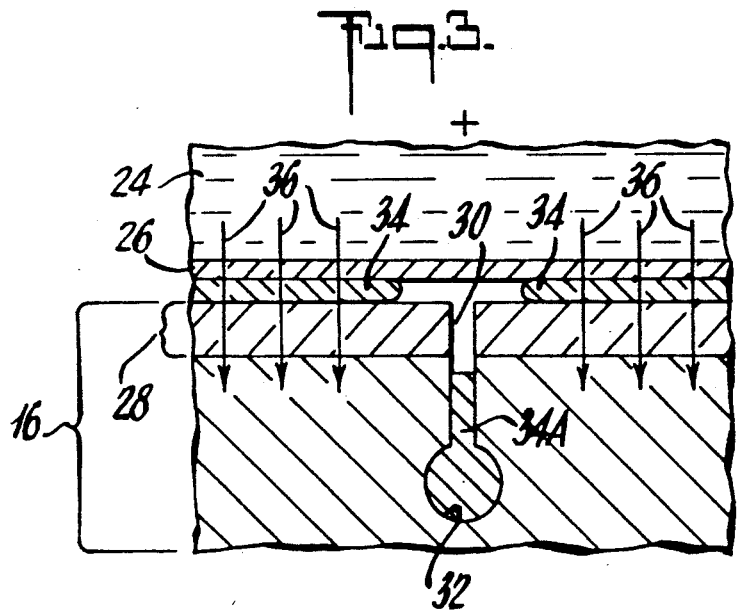
FIG. 3 is the cross-sectional view shown in FIG. 2 with drug delivery being made through the stratum corneum with an exemplary inactive skin shunt and inactive gland.

FIG. 3 illustrates the manner in which the drug or drugs in solution 24 is passed by electro-osmosis through skin 16 via stratum corneum 28 with no flow through shunt duct 30 and gland 32. The delivery mode through skin 16 via stratum corneum 28 occurs by way of a liquid 34 originating with solution 24, which becomes established between membrane 26 and the surface of stratum corneum 28. This phenomenon takes place because liquid 34, which passes by electro-osmotic movement from solution 24 as indicated by arrows 36, provides the path of least resistance for the electrical current.

As best illustrated in FIG. 7, prior art systems of delivery, after a short delay during start-up, provide a relatively low, steady current 38 through skin 16 by way of shunt ducts 30. FIG. 7 illustrates in dashed line graphic models of the prior art and shows the advantages of the present invention. As indicated in FIG. 7, total steady state current 38 is the sum of a current 40 through shunt ducts 30 and a lesser current 44 through stratum corneum 28. The rate of drug delivery through both shunt ducts 30 or stratum corneum 28 is related to the amount of current delivered to each. In general, current 40 causes a steady rate of drug delivery through shunt duct 30 (which is representative of all shunt ducts in the area of reservoir 12) as shown in FIG. 2 and a steady, lesser rate of drug delivery through stratum corneum 28 (as shown in FIG. 3). The total amount of current 38 must be very low since the current density is extremely high because of the small diameters and resulting small total areas of shunt ducts 30 (one thousandth of the skin surface). If the current were increased, irritation and damage to shunt ducts 30 and glands 30 would result because of over-heating and excessive osmotic pressure.

In accordance with the present invention, electrically induced drug delivery can be made primarily through stratum corneum 28 rather than through shunt ducts 30. The advantages of delivery through stratum corneum 28 are several. First, the heating of liquid 34A in shunt ducts 30 can be limited and thus the problem of irritation or damage to shunt ducts 30 is eliminated. Second, because shunt ducts 30 are bypassed for long periods of time, the amount of electrical current passing the drug or drugs into skin 16 by way of stratum corneum 28 can be increased, thus increasing the overall rate of drug delivery. Third, the fact that the area of stratum corneum 28 is about a thousand times greater than the area of shunt ducts 30 results in greater total delivery of the drug or drugs into skin (flux) 16 through stratum corneum 28 and subsequently to the systemic blood of the patient despite the higher resistivity of stratum corneum 28 to the passage of liquids and electricity.

The present invention provides an electro-osmotic drug delivery system that first of all limits liquid 34A that is delivered through shunt ducts 30. FIG. 4 illustrates a drug patch 46 that is made of a uniform or anisotropic semi-dry hydrogel 48 of a semi-dry consistency that limits the amount of liquid that the gel can electro-osmotically pass through shunt ducts 30, particularly by the limitation of lateral liquid movement within gel 48 relative to skin 16. This limitation on the rate of liquid 34A being passed from patch 46 to shunt ducts 30 quickly breaks up liquid 34A in shunt ducts 30, since liquid 34A must be constantly replenished therein. The presence of liquid 34A in the area immediately below the undersurface of drug patch 46 at shunt duct 30 is replenished at such a slow rate that the liquid refills too slowly to make the ducts the electrical shunts paths needed to pass any of current 50 (FIG. 7) and liquid 34A carrying the drug or drugs. Current 50, and therefore liquid 34A with the drug or drugs, passes through stratum corneum 28 as current 51 (FIG. 7) with the rate of drug delivery through stratum corneum 28 being related. FIG. 7 shows total current 50 delivered to the system significantly higher than current 38 delivered by the prior art and a resulting total rate of drug delivery 52 that is likewise significantly higher than prior art total rate of drug delivery 42. The rate of drug delivery through stratum corneum 28 is substantially the same as total rate of drug delivery 52 with an exception to be discussed. It is to be noted, however, that rate of drug delivery 52 is higher than prior art rate of delivery 42 also because of the much greater area of stratum corneum 28 relative to shunt ducts 30 under patch 46, despite the fact that stratum corneum 28 is much more resistant to the passage of the liquid carrying the drug or drugs than shunt ducts 30.

Periodically, however, liquid 34A will build up in shunt ducts 30 in sufficient quantity to create an electrical path so that a electrical current, shown as pulsations 54 in FIG. 7, will be delivered through shunt ducts 30 in the manner shown in FIG. 2. This causes a divergence of current 50 between shunt ducts 30 and stratum corneum 28 so that periodic pulsations 54 of current at shunt ducts 30 occur at long intervals of time, typically an hour. The periodicity of pulsations 54 can be controlled by the degree of dryness of patch 46 combined with a particular current 50. Pulsations 54 represent an increased current through shunt ducts 30; and current down blips 56 (FIG. 7) represent a decreased current through stratum corneum 28. The combination results in periodic slight increases in total drug delivery to the blood represented in FIG. 7 by up blips 58. The slight increase in total delivery represented by up blips 58 as the result of a temporary increase in the rate of delivery through shunts 30, during which time stratum corneum 28 continues to deliver the drug or drugs en transit, is similar to the functioning of a passive osmotic patch. Delivery of liquid 34A with the drug or drugs is related to the current passages 51 and 54. Because of the relative dryness of drug patch 46, liquid 34A periodically depletes patch 46 in the area over shunt ducts 30 in the manner previously described. Both current 54 and drug delivery through shunt ducts 30 cease and the exclusive passage of current 51 and exclusive delivery of the drug or drugs returns to stratum corneum 28. Thus, the invention also provides for periodic "blow outs" of liquid 34A from shunt ducts 30.

An alternate embodiment of the invention is a wet patch 60 illustrated in FIG. 5. Wet patch 60 includes a solution 62 that includes a drug or drugs to be delivered enclosed by a semi-permeable membrane 64, which passes only a limited amount of liquid 34, particularly in a direction lateral to skin 16 so that the area over shunt ducts 28 under membrane 64 is generally devoid, or starved, of liquid. The results are the same as discussed above in relation to semi-dry patch 46 in FIGS. 4 and 7.

FIG. 6 illustrates a water repellent, or hydrophobic layer 67 applied to the undersurface of a matrix patch 66. Hydrophobic layer 67 inhibits the movement of liquid 34 from matrix patch 66 to shunt ducts 30 and breaks the column of liquid 34A in shunt ducts 30. Any of a number of hydrophobic materials may be used, such as silicon, fluorocarbons, paraffins, and the like. The results of the use of hydrophobic layer 67 are the same as discussed above in relation to FIG. 4.

FIG. 9 is a model graph that illustrates a drug delivery system A of a skin comprising all stratum corneum and devoid of skin shunts, for example, rabbit skin. In drug delivery system A the drug delivery increases as the current delivery to the stratum corneum increases. Skin damage occurs above a particular current density, which in effect defines the maximum flux, that is, the quantity of drug delivered per unit of time per unit of skin surface. This is illustrated in system A by $I_{max}A$. FIG. 9 also illustrates a drug delivery system B of a theoretical skin comprising all shunt ducts and devoid of a stratum corneum. In drug delivery system B the drug delivery increases at a very high rate, then quickly decreases as the current increases, as damage to the shunts occurs at a current density $I_{max}B$. Current density $I_{max}B$ is much lower than $I_{max}A$, which in indicative of a negligible delivery through stratum corneum 28. FIG. 9 also illustrates a drug delivery system C, which is the present invention as described in relation to FIGS. 4–6 and which delivers the drug or drugs to the human skin having both a stratum corneum 28 and skin shunt ducts 30. In the inventive system, shunt ducts 30 are theoretically bypassed in favor of delivery of current and drugs mostly through stratum corneum 28. The advantage of system C is that in a skin having shunt ducts 30 almost the same overall current and rate of drug delivery as to a skin having no shunt ducts is possible. This is illustrated in FIG. 9 by the maximum current density of system C, $I_{max}C$, being about the same as $I_{max}A$. Both systems A and C allow high current densities so that the overall drug delivery can be increased despite the greater resistivity of the stratum corneum to the passage of current and drugs, as illustrated in system C.

The periodic blow-outs of shunt ducts 30 as indicated by blips 54 can be triggered by periodic increases in the total current being delivered to the patch. A current conditioning device, preferably an oscillator 68, can be employed in series in the electrical circuit as shown in schematic representation in FIG. 8. Oscillator 68 provides periodic current increases over current 50 at predetermined intervals, shown in dotted line in FIG. 7 as current pulsations 70, which are indicated at one hour intervals. The embodiments of the invention shown in FIGS. 4–6 break up the capillary liquid film present between the patch and skin 16, thus preventing lateral liquid movement from replenishing the depleting amount of liquid in shunts 30 promoting an earlier breakage of the liquid or film by causing a high water surface contact angle, which is observed as beaded droplets. The liquid columns in ducts 30 are thus broken more easily. The liquid columns reestablish with great difficulty, thus lowering the frequency of pulsations and thus lowering the total amount of current that ducts 30 are exposed to. Also, the breaking up the capillary liquid present between the patch add skin 16 will delay or prevent the reestablishment of continuous liquid columns in ducts 30. Selected current pulsations 70 are such that when combined with the liquid-movement inhibiting features of the drug patches described in relation to FIGS. 4–6, shunt ducts 30 to replenished liquid 34A at selected periodic time intervals. Shunt ducts 30 are thereupon emptied of liquid 34A by the combination of the effect of the semi-dry drug patches, current 50, a molecular hydrophobic layer, and current pulsations 70. The increased level of current, that is, current pulsations 54, accelerate the emptying of shunt ducts 30 of liquid 34A at long time intervals in accordance with the selected time intervals as designed for by the selection of the semi-dry patches and the level of current 50, with the time intervals being shown as one hour for purposes of exposition only.

The long-time intervals between pulsations, shown for purposes of exposition as 1 hour, can vary generally between a number of minutes and a number of hours.

Liquid 34A is preferably aqueous. It is also within the scope of this invention that liquid 34 comprises hydrophilic mixtures containing alcohols, glycols, and the like, or oil colloidal suspensions; or hydrophilic compounds, such as alcohols, glycols and the like, oil colloidal dispersions of water in oil or oil in water, or even liquids wherein oil is the continuous phase.

Although the present invention has been described in some detail by way of illustration and example for purposes of clarity and understanding, it will, of course, be understood that various changes and modifications may be made in the form, details, and arrangements of the parts without departing from the scope of the invention as set forth in the following claims.

What is claimed is:

1. An electro-osmotic transdermal drug delivery system for passing at least one drug for delivery to the systemic blood of a living creature through skin thereof having a plurality of sweat and sebaceous capillary ducts opening to the surface of the stratum corneum, comprising: drug storage means disposed in use juxtaposed to the surface of a given area of the skin and having therein a drug-containing electrolytic liquid containing in solution or suspension at least one drug to be delivered by electro-osmotic motion into the skin, an electrical circuit connected to the drug storage means and having an electrode electrically in contact with the skin when the system is in use, a power source in said electrical circuit connected to the drug storage means and the electrode for applying an electrical current to the drug storage means for moving drug-containing electrolytic liquid by electro-osmotic motion into the skin, means for maximizing delivery of the drug-containing electrolytic liquid through the stratum corneum in said given area of the skin by inhibiting of flow paths for the electrolytic liquid into the capillary ducts and for inhibiting the filling thereof to the surface of the stratum corneum comprising means for inhibiting delivery of said electrolytic liquid into the capillary ducts in said given area of the skin and electrical means in said circuit for effectively inhibiting retention of electrolytic liquid in the capillary ducts thereby to inhibit the capillary ducts from functioning as paths of lesser electrical resistance than the stratum corneum and as shunt ducts for flow and delivery of the drug containing electrolytic liquid in said given area of the skin rather than through the stratum corneum of said given area of the skin.

2. An electro-osmotic transdermal drug delivery system according to claim 1, in which said means for inhibiting delivery of electrolytic liquid into the capillary ducts comprises means in the drug storage means for inhibiting lateral movement of the electrolytic liquid thereby inhibiting development of flow paths into the capillary ducts as the liquid moves in electro-osmotic motion due to current flow.

3. An electro-osmotic transdermal drug delivery system for delivery of at least one drug to the blood system of a living creature through skin thereof having a plurality of sweat and sebaceous capillary ducts opening to the surface of the stratum corneum, comprising: a drug storage reservoir positionable in use juxtaposed to the external surface of an area of the skin through which delivery of at least one drug is to be effected, said drug storage reservoir having therein a drug-containing electrolytic liquid containing at least one drug in solution or suspension and to be delivered by electro-osmotic movement of the drug-containing electrolytic liquid through the skin, an electrical circuit having means for effecting an electrical connection to the drug storage reservoir and having an electrode electrically in contact with the skin external of said area thereof when the system is in use, means in said electrical circuit comprising a battery for effecting electro-osmotic movement of the drug-containing electrolytic liquid through the skin in said area thereof, means in said circuit for inhibiting functioning of the capillary ducts as electrical and flow shunt capillary ducts for delivery of drug-containing electrolytic liquid through the skin in said area of the skin relative to which the drug storage reservoir is juxtaposed when the system is in use, whereby delivery of the drug-containing electrolytic liquid when the system is in use is principally through the stratum corneum of the skin in said area of the skin, and said means in said electrical circuit for effecting electro-osmotic movement of said electrolytic liquid comprising a battery and electrical means coactive with said battery for developing periodic positive current pulses only of a higher value than that of direct current applied through said electrical circuit.

4. An electro-osmotic transdermal delivery system according to claim 3, in which said means for developing said periodic positive current pulses comprises an oscillator in series with said battery.

* * * * *